US009863856B2

(12) United States Patent
Wang et al.

(10) Patent No.: US 9,863,856 B2
(45) Date of Patent: Jan. 9, 2018

(54) METHOD FOR IMAGING NANOSTRUCTURES WITH OPTICAL MICROSCOPY

(71) Applicants: Tsinghua University, Beijing (CN); HON HAI PRECISION INDUSTRY CO., LTD., New Taipei (TW)

(72) Inventors: Jiang-Tao Wang, Beijing (CN); Tian-Yi Li, Beijing (CN); Qing-Yu Zhao, Beijing (CN); Kai-Li Jiang, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 100 days.

(21) Appl. No.: 14/604,348

(22) Filed: Jan. 23, 2015

(65) Prior Publication Data

US 2015/0211980 A1    Jul. 30, 2015

(30) Foreign Application Priority Data

Jan. 25, 2014   (CN) .......................... 2014 1 0034579

(51) Int. Cl.
*G01N 1/28*   (2006.01)
*G02B 21/24*  (2006.01)
(Continued)

(52) U.S. Cl.
CPC ........... *G01N 1/28* (2013.01); *G01N 15/1463* (2013.01); *G02B 21/0004* (2013.01);
(Continued)

(58) Field of Classification Search
CPC .... G01N 1/28; G01N 1/4022; G01N 15/1463; G01N 15/065; G01N 2015/0038; G02B 21/0004; G02B 21/00; G02B 21/24
(Continued)

(56) References Cited

U.S. PATENT DOCUMENTS 5,315,344 A     5/1994  Clark et al.
6,334,329 B1 *  1/2002  Weller ...................... F25D 3/08
                                                            62/371
(Continued)

FOREIGN PATENT DOCUMENTS

CN        2086608        10/1991
CN        2086608 U      10/1991
(Continued)

OTHER PUBLICATIONS

Coskun Kocabas, Seung-Hyun Hur, Anshu Gaur, Matthew A. Meitl, Moonsub Shim, and John A. Rogers, "Guided Growth of Large-Scale, Horizontally Aligned Arrays of Single-Walled Carbon Nanotubes and Their Use in Thin-Film Transistors", Nov. 2005, Wiley-VCH, Small 2005, vol. 1, Issue 11, pp. 1110-1116. http://onlinelibrary.wiley.com/doi/10.1002/sml.*
(Continued)

*Primary Examiner* — William R Alexander
(74) *Attorney, Agent, or Firm* — ScienBiziP, P.C.

(57) ABSTRACT

A method for observing nanostructures by optical microscopy is provided. Firstly, a sample with a nanostructure and a vapor-condensation-assisted optical microscopy system are provided. The vapor-condensation-assisted optical microscopy system comprises a vapor-condensation-assisted device and an optical microscope comprising a stage. The vapor-condensation-assisted device is used to provide a vapor to sample on the stage in application. Secondly, locating the sample is located on the stage. Thirdly, a vapor
(Continued)

is applied to the sample to observe the sample via the optical microscopy system.

20 Claims, 8 Drawing Sheets

(51) Int. Cl.
*G01N 15/14* (2006.01)
*G02B 21/00* (2006.01)
*G01N 15/06* (2006.01)
*G01N 15/00* (2006.01)

(52) U.S. Cl.
CPC ........... *G02B 21/24* (2013.01); *G01N 15/065* (2013.01); *G01N 2015/0038* (2013.01); *G02B 21/00* (2013.01)

(58) Field of Classification Search
USPC .................................................. 359/391, 368
See application file for complete search history.

(56) References Cited

U.S. PATENT DOCUMENTS

| | | | |
|---|---|---|---|
| 6,392,745 B1 | 5/2002 | Mavliev et al. | |
| 2014/0287150 A1* | 9/2014 | Miljkovic | B01D 5/0042 427/458 |

FOREIGN PATENT DOCUMENTS

| | | |
|---|---|---|
| CN | 201785638 | 4/2011 |
| CN | 102221194 | 10/2011 |

OTHER PUBLICATIONS

Yongfang Zhong, Anthony M. Jacobi, John G. Georgiadis, "Condensation and Wetting Behavior on Surfaces With Micro-Structures: Super-Hydrophobic and Super-Hydrophilic" (2006). International Refrigeration and Air Conditioning Conference. Paper 828. Purdue University, Purdue e-Pubs, pp. 1-8. http://docs.lib.purdue.edu/iracc/828.*

* cited by examiner

METHOD FOR IMAGING NANOSTRUCTURES WITH OPTICAL MICROSCOPY

RELATED APPLICATIONS

This application claims priority to Chinese Patent Application No. 201410034579.3 filed on Jan. 25, 2014 in the China Intellectual Property Office, the contents of which are incorporated by reference herein.

FIELD

The subject matter herein generally relates to an optical microscopy system and method for imaging nanostructures with the optical microscopy system.

BACKGROUND

An accurate and efficient imaging of nanostructures can significantly deepen our understanding of the microscopic world and shed light on prospective applications. Compared with scanning electron microscope (SEM), transmission electron microscope (TEM), atomic force microscope (AFM), scanning tunneling microscope (STM), etc., it is very easy to operate an optical microscope and quite convenient to integrate it with other facilities. However, nanomaterials or nanostructures such as carbon nanotubes (CNTs) cannot be directly observed by optical microscope, because their nanoscale dimensions are much smaller than the wavelength of visible light.

Therefore the visualization of nanomaterials, especially of CNTs by optical microscopy is highly desirable and has long been attempted.

BRIEF DESCRIPTION OF THE DRAWINGS

Many aspects of the present optical microscopy system can be better understood with references to the following drawings. The components in the drawings are not necessarily drawn to scale, the emphasis instead being placed upon clearly illustrating the principles of the present optical microscopy system.

Figure 1:
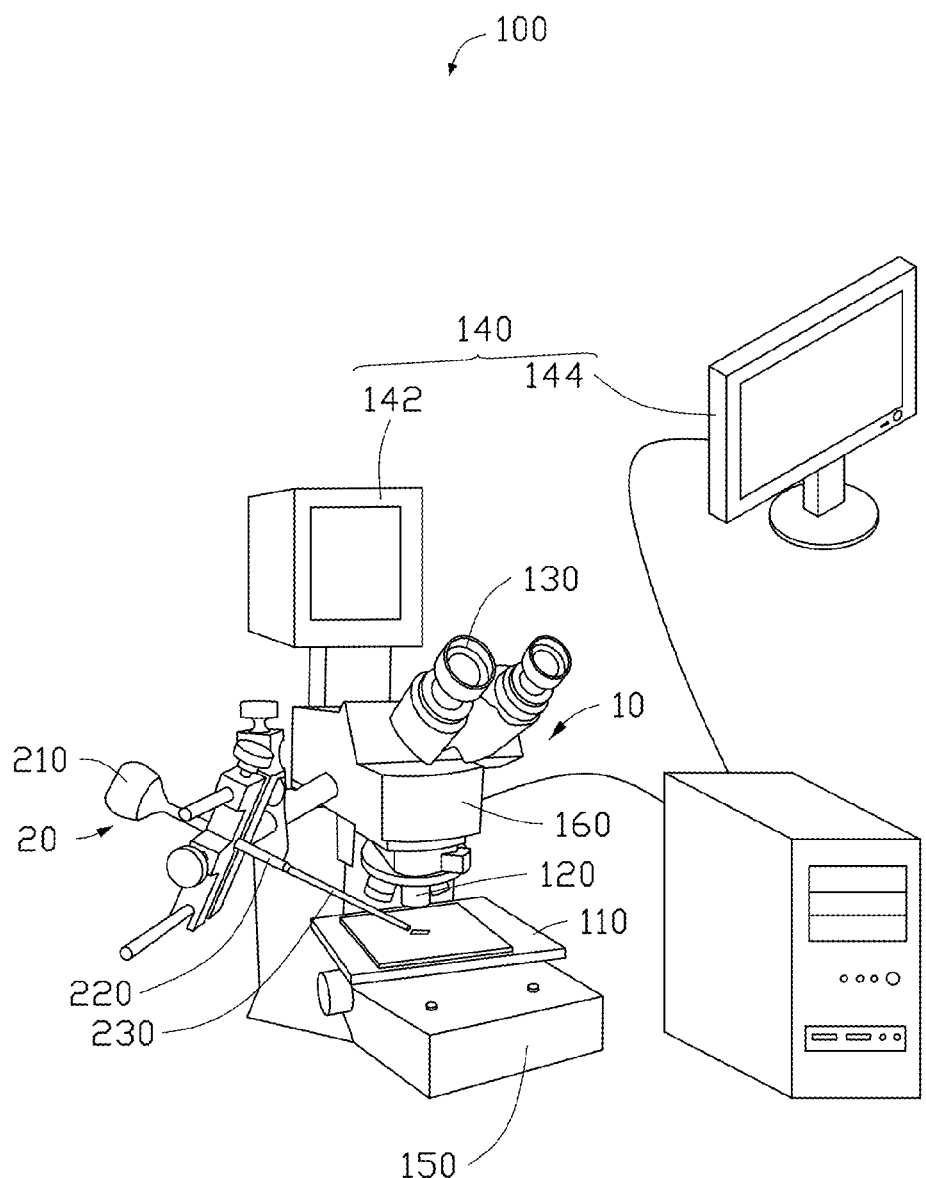
FIG. 1 is a schematic view of an optical microscopy system in accordance with an embodiment.

Corresponding reference characters indicate corresponding parts throughout the several views. The exemplifications set out herein illustrate at least one present embodiment of optical microscopy system and method for using the same, in at least one form, and such exemplifications are not to be construed as limiting the scope of the disclosure in any manner.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

References will now be made to the drawings to describe, in detail, various embodiments of the present epitaxial structures and methods for making the same.

Referring to FIG. 1, an optical microscopy system 100 is provided according to one embodiment. The optical microscopy system 100 comprises an optical microscope 10 and a vapor-condensation-assisted device 20. The optical microscope 10 can be one of various optical microscopes in existing technology. The vapor-condensation-assisted device 20 is used to provide vapor.

In one embodiment, the optical microscope 10 comprises stage 110, objective lenses 120, eyepiece 130, and an image collecting system 140, a light source system 150 and focus adjusting system 160.

The stage 110 is a platform below the objective lenses 120 which supports the specimen being viewed. The objective leases 120 are usually in a cylinder housing containing a glass single or multi-element compound lens. The optical microscope 10 can comprises one or more objective lenses 120 that collect light from the specimen. In one embodiment, there are around three objective lenses 120 screwed into a circular nose piece which may be rotated to select the required objective lens 120. These arrangements are designed to be par focal, which means that when one changes from one lens to another on a microscope, the specimen stays in focus. The image collecting system 140 comprises a computer 144 and a camera 142. The focus adjusting system 160 comprises focus knobs to move the stage 110 up and down with separate adjustment for coarse and fine focusing. Many sources of light can be used as the light source system 150. At its simplest, daylight can be directed via a mirror.

Figure 2:
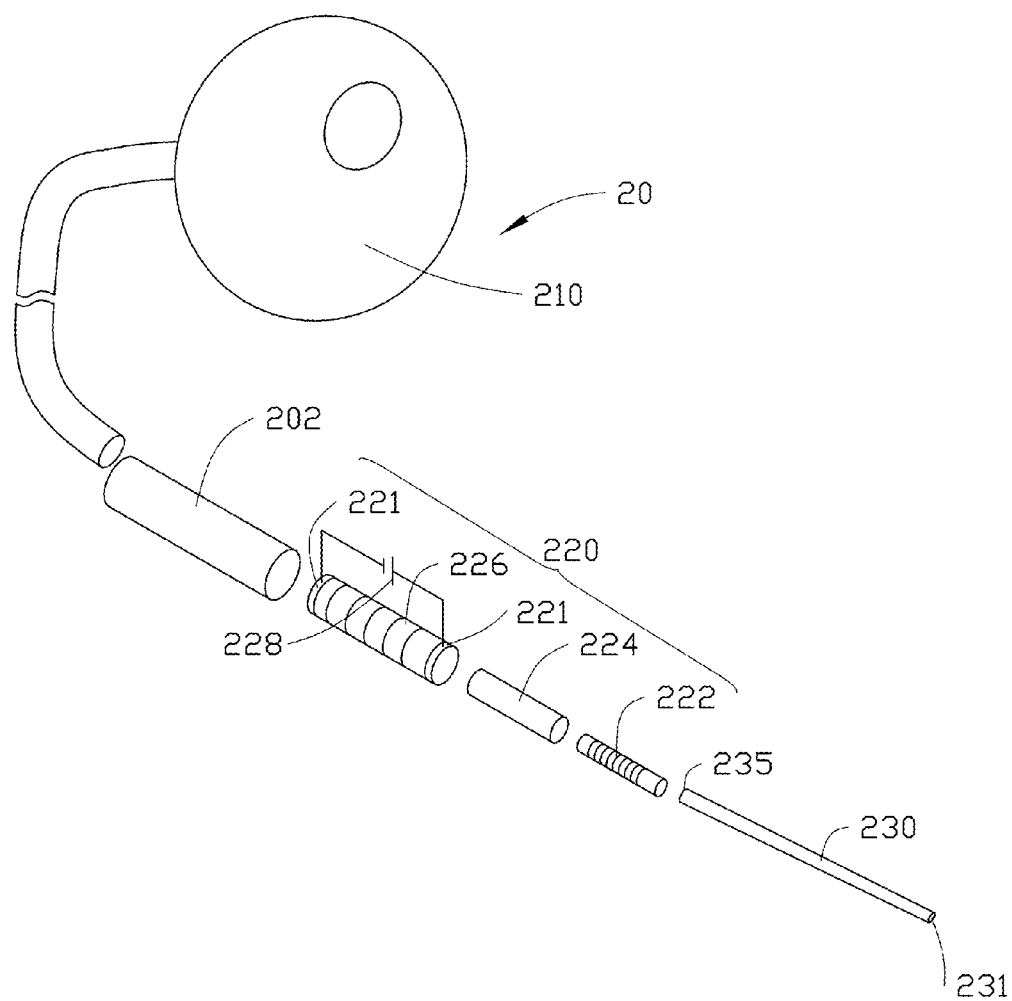
FIG. 2 is an exploded view of a vapor-condensation-assisted device in accordance with one embodiment.

Referring to FIG. 2, the vapor-condensation-assisted device 20 comprises an air blowing device 210, a vapor producing device 220 and a guide pipe 230. The air blowing device 210 is connected to the vapor producing device 220 and can blow air into the vapor producing device 220. The vapor producing device 220 is connected to the guide pipe 230. The air can blow from the air blowing device 210 into the vapor producing device 220 and out of the guide pipe 230. The vapor produced in the vapor producing device 220 can be blown to the specimen on the stage 110 by the blowing air from the air blowing device 210.

The air blowing device 210 can be a flexible bulb that is able to inhale or exhale the air by pressing. The air bowling device 210 is connected to the vapor producing device 220. The air can be blown into the vapor producing device 220 by the air blowing device 210. In one embodiment, the air blowing device 210 is a rubber suction bulb.

The vapor producing device 220 comprises a liquid absorbing material 222, a hollow tube 224, and heating layer 226 and a power source 228. The liquid absorbing material 222 is located in the hollow tube 224, but does not affect the ventilation performance of the hollow tube 224. A liquid material is absorbed by the liquid absorbing material 222. The heating layer 226 is surrounded the out surface of the hollow tube 224 and electrical connected to the power source 228. The heating layer 226 is used to heat the liquid absorbing material 222 located in the hollow tube 224. The liquid material turns into vapor when the liquid absorbing material 222 is heated.

A material of the hollow tube 224 is not limited, and can be soft or hard materials. The hard material can be ceramic, glass, or quartz. The soft material can be resin, rubber, plastic or flexible fiber. The cross section shape of the hollow tube 224 is also unlimited, and can be round, arc, or rectangle. In one embodiment, this example, the hollow tube 224 is a hollow ceramic tube with a circular cross section.

The liquid absorbing material 222 has good absorption performance. The liquid absorbing material 222 can be cotton, non-woven fabrics and high absorbent resin. In one embodiment, the liquid absorbing material 222 is attached to the inner surface of the hollow tube 224.

The heating layer 226 is disposed on an outer surface of the hollow tube 224. The heating layer 226 comprises a carbon nanotube structure. The carbon nanotube structure includes a plurality of carbon nanotubes uniformly distributed therein, and the carbon nanotubes therein can be combined by van der Waals attractive force therebetween. The carbon nanotube structure can be a substantially pure structure of the carbon nanotubes, with few impurities. The carbon nanotubes can be used to form many different structures and provide a large specific surface area. The heat capacity per unit area of the carbon nanotube structure can be less than $2 \times 10^{-4}$ J/m$^2$·K. Typically, the heat capacity per unit area of the carbon nanotube structure is less than $1.7 \times 10^{-6}$ J/m$^2$·K. As the heat capacity of the carbon nanotube structure is very low, and the temperature of the heating element 16 can rise and fall quickly, which makes the heating layer 226 have a high heating efficiency and accuracy. As the carbon nanotube structure can be substantially pure, the carbon nanotubes are not easily oxidized and the life of the heating layer 226 will be relatively long. Further, the carbon nanotubes have a low density, about 1.35 g/cm$^3$, so the heating layer 226 is light. As the heat capacity of the carbon nanotube structure is very low, the heating layer 226 has a high response heating speed. As the carbon nanotube has large specific surface area, the carbon nanotube structure with a plurality of carbon nanotubes has large specific surface area. When the specific surface of the carbon nanotube structure is large enough, the carbon nanotube structure is adhesive and can be directly applied to the surface outer surface of the hollow tube 224.

The carbon nanotubes in the carbon nanotube structure can be arranged orderly or disorderly. The term 'disordered carbon nanotube structure' refers to a structure where the carbon nanotubes are arranged along many different directions, and the aligning directions of the carbon nanotubes are random. The number of the carbon nanotubes arranged along each different direction can be almost the same (e.g. uniformly disordered). The disordered carbon nanotube structure can be isotropic. The carbon nanotubes in the disordered carbon nanotube structure can be entangled with each other.

The carbon nanotube structure including ordered carbon nanotubes is an ordered carbon nanotube structure. The term 'ordered carbon nanotube structure' refers to a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions). The carbon nanotubes in the carbon nanotube structure can be selected from a group consisting of single-walled, double-walled, and/or multi-walled carbon nanotubes.

The carbon nanotube structure can be a carbon nanotube film structure with a thickness ranging from about 0.5 nanometers to about 1 millimeter. The carbon nanotube film structure can include at least one carbon nanotube film. The carbon nanotube structure can also be a linear carbon nanotube structure with a diameter ranging from about 0.5 nanometers to about 1 millimeter. The carbon nanotube structure can also be a combination of the carbon nanotube film structure and the linear carbon nanotube structure. It is understood that any carbon nanotube structure described can be used with all embodiments. It is also understood that any carbon nanotube structure may or may not employ the use of a support structure.

Figure 3:
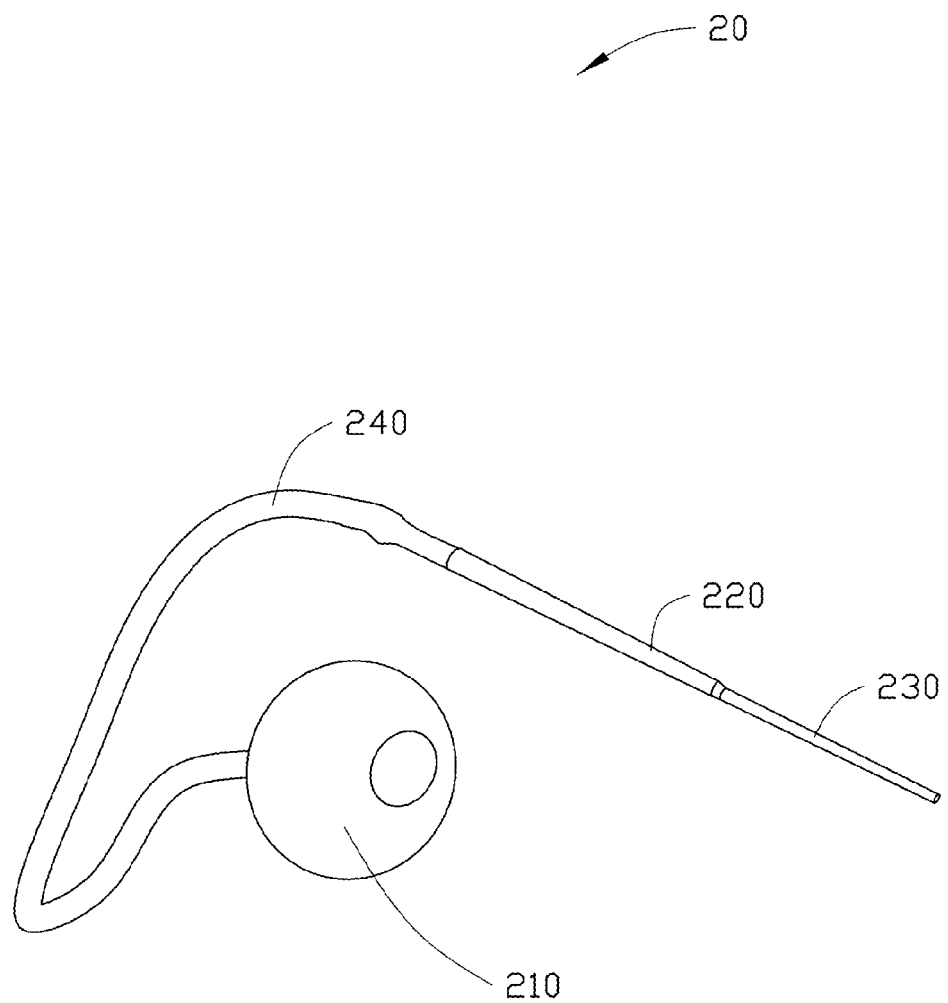
FIG. 3 is a schematic view of the vapor-condensation-assisted device in accordance with FIG. 2.

In one embodiment, the carbon nanotube structure includes at least one drawn carbon nanotube film. A film can be drawn from a carbon nanotube array, to form a drawn carbon nanotube film. The drawn carbon nanotube film includes a plurality of successive and oriented carbon nanotubes joined end-to-end by van der Waals attractive force therebetween. The drawn carbon nanotube film is a free-standing film. Each drawn carbon nanotube film includes a plurality of successively oriented carbon nanotube segments joined end-to-end by van der Waals attractive force therebetween. Each carbon nanotube segment includes a plurality of carbon nanotubes parallel to each other, and combined by van der Waals attractive force therebetween. As can be seen in FIG. 3, some variations can occur in the drawn carbon nanotube film. The carbon nanotubes 145 in the drawn carbon nanotube film are oriented along a preferred orientation. The carbon nanotube film can be treated with an organic solvent to increase the mechanical strength and toughness of the carbon nanotube film and reduce the coefficient of friction of the carbon nanotube film. A thickness of the carbon nanotube film can range from about 0.5 nanometers to about 100 micrometers.

The vapor producing device 220 further comprises two electrodes 221 located on and electrically connected to the heating layer 226. Furthermore, it is imperative that the two spaced electrodes 221 are separated from each other to prevent short circuiting of the electrodes. The two electrodes 221 can be directly electrically attached to the heating layer 226 by, for example, a conductive adhesive (not shown), such as silver adhesive. Because, some of the carbon nanotube structures have large specific surface area and are adhesive in nature, in some embodiments, the two electrodes 221 can be adhered directly to heating layer 226. It should be noted that any other bonding ways may be adopted as long as the two electrodes 221 are electrically connected to the heating layer 226. The shape of the two electrodes 221 are not limited and can be lamellar, rod, wire, and block among other shapes.

The two electrodes 221 can be conductive films. A material of the two electrodes 221 can be metal, alloy, indium tin oxide (ITO), antimony tin oxide (ATO), conductive silver glue, conductive polymers or conductive carbon nanotubes. The metal or alloy materials can be aluminum, copper, tungsten, molybdenum, gold, titanium, neodymium, palladium, cesium or any combination of the alloy. In one embodiment, the electrode 221 is a palladium film with a thickness of 20 nanometers.

The power source 228 can be AC or DC power. The power source 228 is electrically connected to the two electrodes 221. When a voltage is applied to heating layer 226 via the two electrodes 221, the carbon nanotube structure of the heating layer 226 radiates heat at a certain wavelength. The temperature of the heating layer 226 ranges from 50° C. to 500° C., the liquid material in the liquid absorbing material 222 turns to vapor.

The vapor producing device 220 can further comprises a protecting layer 202 attached to the exposed surface of the heating layer 226. The protecting layer 202 can protect the heating layer 226 from the environment. A material of the protecting layer 202 can be an insulated material, such as resin, plastic or rubber. A thickness of the protecting layer 202 can range from about 0.5 μm to about 2 mm.

The guide pipe 230 comprises a first opening 231 and a second opening 235 opposite to the first opening 231. The diameter of the first opening 231 is smaller than the diameter of the second opening 235. Air can flow from the first opening 231 to the second opening through the guide pipe 230. The second opening 235 is sealed connected to the vapor producing device 220. The material of the guide pipe 230 is not limited, and can be soft or hard materials. The hard material can be ceramic, glass, or quartz. The soft material can be resin, rubber, plastic or flexible fiber. The cross section shape of the hollow tube 224 is also unlimited, and can be round, arc, or rectangle. In one embodiment, this example, the guide pipe 230 is a hollow ceramic tube with a circular cross section.

The air blowing device 210, the vapor producing device 220 and the guide pipe 230 are integrated with each other. The air blowing device 210 can push the air through the vapor producing device 220 and the guide pipe 230, from the first opening 231 to the sample on the stage 110.

Referring to FIG. 3, the vapor-condensation-assisted device 20 can further comprises an additional pipe 240. The additional pipe 240 is located between the vapor producing device 220 and the air blowing device 210. The vapor producing device 220 is connected to the air blowing device 210 via the additional pipe 240. The material of the additional pipe 240 is not limited, and can be soft or hard materials. The hard material can be ceramic, glass, or quartz.

The soft material can be resin, rubber, plastic or flexible fiber. The stability of air flow can be enhanced by the additional pipe 240. In one embodiment, the additional pipe 240 is made of rubber, and 50 centimeters long.

Figure 4:
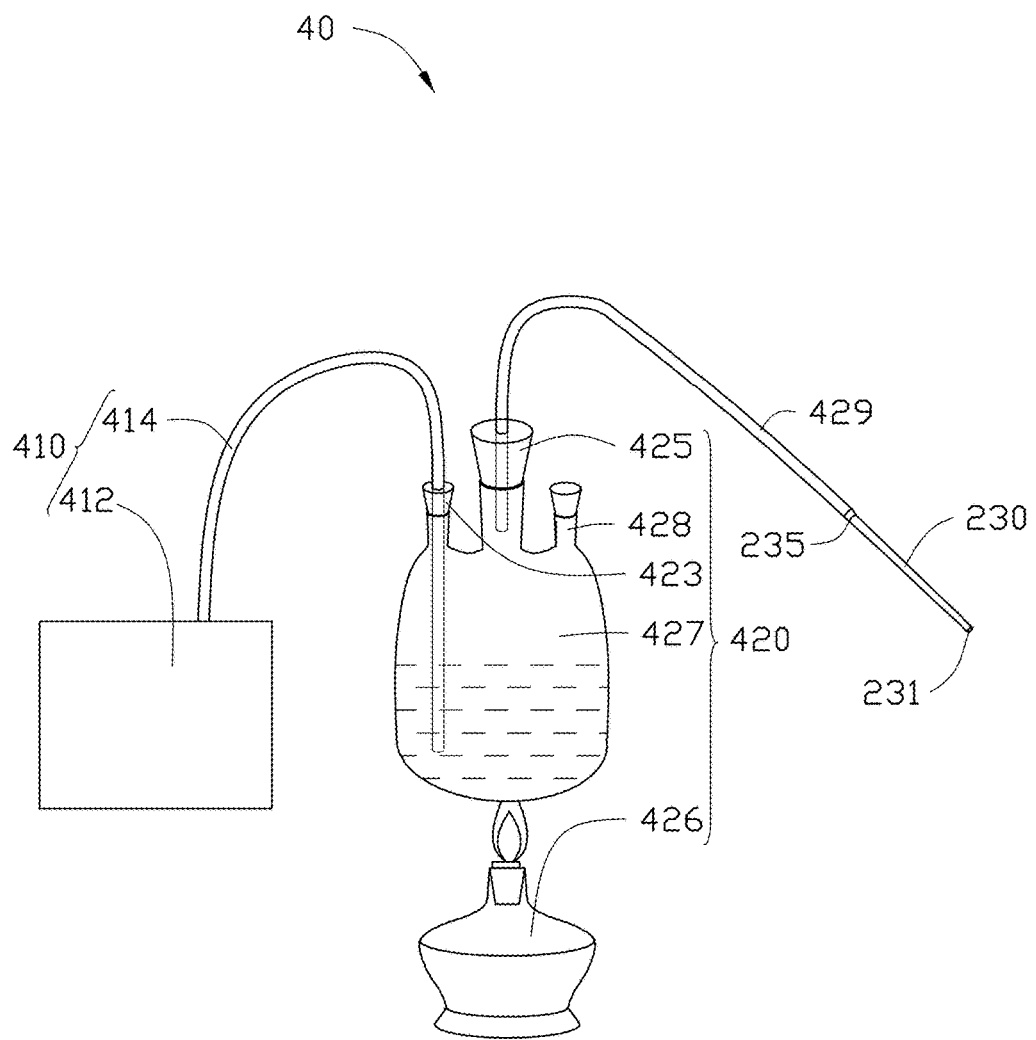
FIG. 4 shows a schematic view of a vapor-condensation-assisted device in accordance with one embodiment.

Referring to FIG. 4, a vapor-condensation-assisted device 40 according to another embodiment is provided.

The vapor-condensation-assisted device 40 comprises an air blowing device 410, a vapor producing device 420 and a guide pipe 230. The air blowing device 410 comprises a blowing machine 412 and a first connecting pipe 414. First end of the first connecting pipe 414 is connected to the blowing device 410 and used to exhaust the air blowing from the air blowing device 410. Second end of the first connecting pipe 414 is connected to the vapor producing device 420.

The vapor producing device 420 comprises a three neck flask 427 and a second connecting pipe 429. The three neck flask 427 comprises an air inlet 423, an outlet 425 and a liquid inlet 428. A liquid is held in the three neck flask 427. First end of the first connecting pipe 414 is connected to the blowing device 410 and used to exhaust the air blowing from the air blowing device 410. Second end of the first connecting pipe 414 is inserted in the three neck flask 427 through the air inlet 423. Another end of the first connecting pipe 414 is under the liquid surface contained in the three neck flask 427. First end of the second connecting pipe 429 is inserted into the three neck flask 427 through the outlet 425, and is above the liquid surface contained in the three neck flask 427. Second end of the second connecting pipe 429 is sealed connected to the second opening 235 of the guide pipe 230. The liquid inlet 428 is used to pour liquid into the three neck flask 427. When the air is blew into the three neck flask 427 under the liquid surface, liquid particles would get into the second connecting pipe 429 with the air into the second connecting pipe 429. Thus, vapor can be delivered to the stage 110 by the guide pipe 230.

Further, the vapor-condensation-assisted device 40 can comprise a heating device 426 to heat the three neck flask 427 which can help the vapor production. In one embodiment, the heating device 426 is a spirit lamp.

Figure 5:
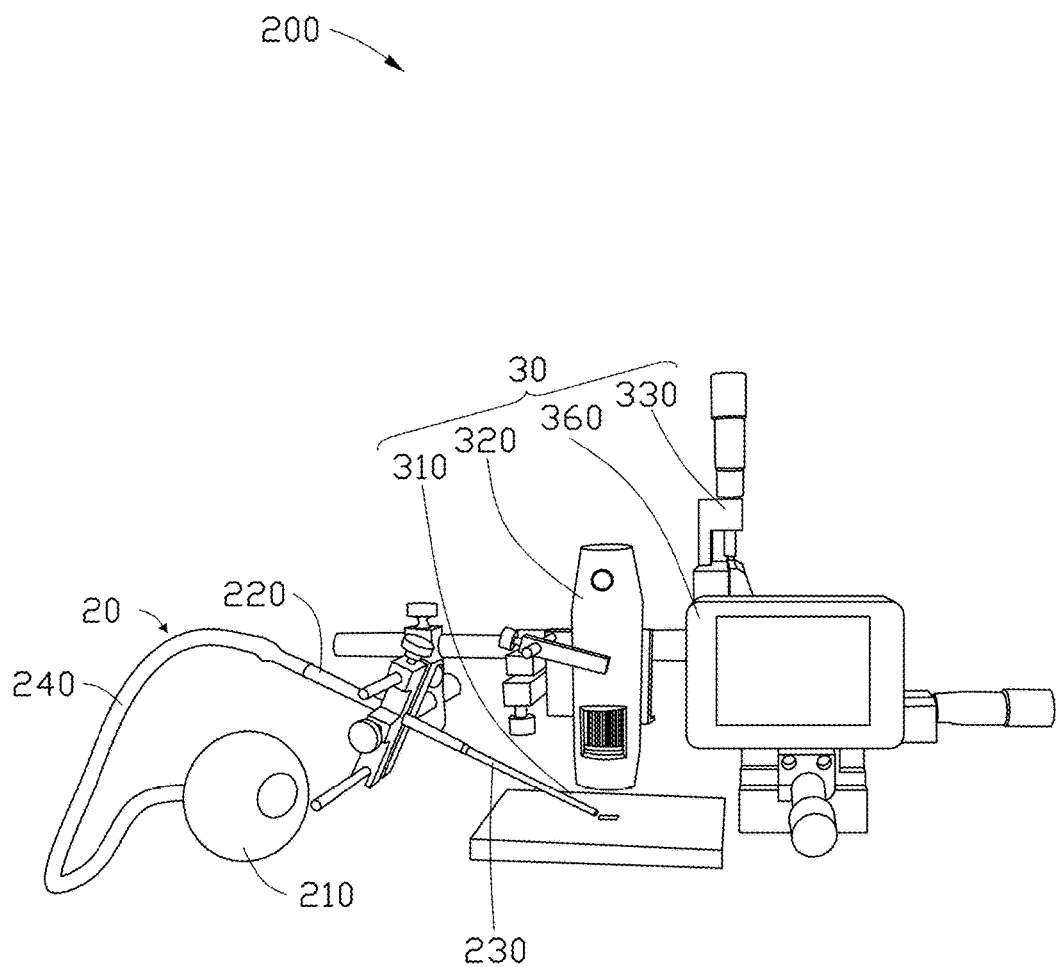
FIG. 5 is a schematic view of an optical microscopy system in accordance with an embodiment.

Referring to FIG. 5, an optical microscopy system 200 is provided according to one embodiment. The optical microscopy system 200 comprises an optical microscope 30 and a vapor-condensation-assisted device 20.

The optical microscope 30 comprises an observing device 320, an image processing device 360, a support frame 330 and a stage 310. The guide pipe 230 of the vapor-condensation-assisted device 20, the observing device 320, and the image processing device 360 are fixed on the support frame 330. The observing device 320 integrated eyepieces, objective lenses, focus knobs, and charge-coupled device (CCD). An image caught by the observing device 320 can be send to the image processing device 360, and display on the screen of the image processing device 360. The optical microscopy system 200 is simple and very low-cost.

A method for observing nanostructures by the optical microscopy system 100, 200 according to the embodiments is provided. The method comprises the steps of:

S1, providing a sample 60 with a nanostructure;

S2, locating the sample 60 on the stage 110, 310 of the optical microscopy system 100, 200; and S3, applying a vapor to the sample 60 to observe the sample 60 via the optical microscopy system 100, 200.

Figure 6:
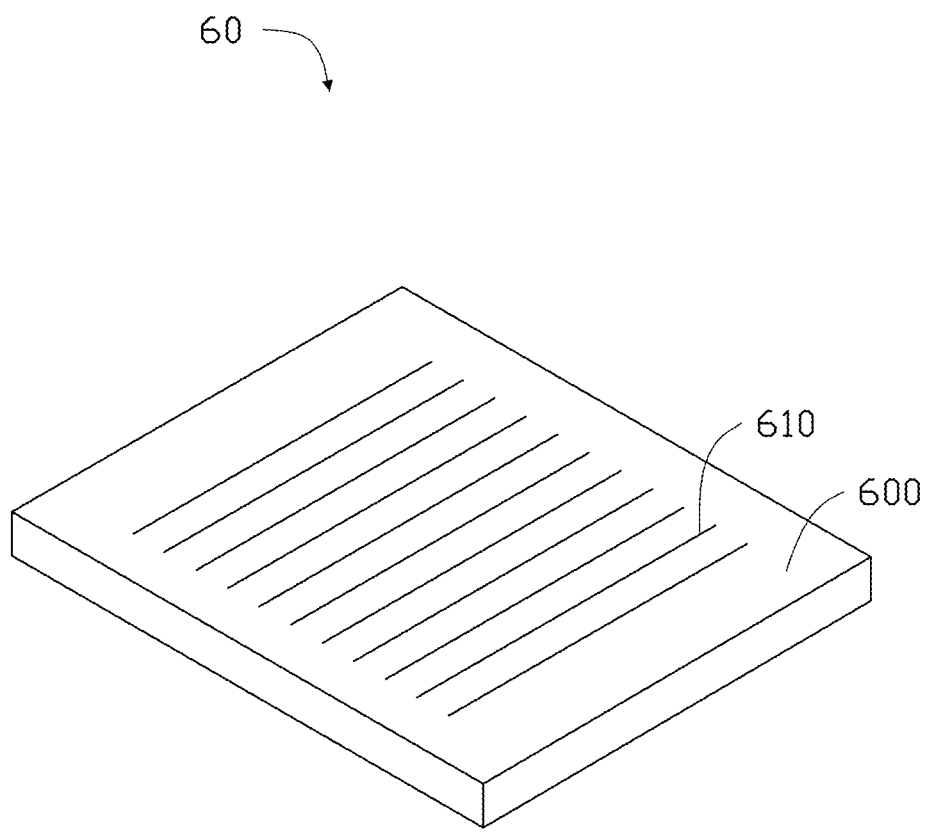
FIG. 6 is a schematic view of carbon nanotubes on a substrate.

In S1, the sample 60 can be any patterns with nanostructures on a substrate. In one embodiment, the sample 60 comprises carbon nanotubes 610 horizontally aligned on a substrate 600 as shown in FIG. 6. The carbon nanotubes 610 are parallel to the surface of the substrate 600. The substrate 600 is a silicon substrate.

In S2, the sample 60 can be located on a slide first and then the slide is put on the stage 110, 310. The substrate 600 can be observed by adjusting the focusing mechanism of the optical microscopy system 100, 200. The sample 60 can not be observed by the optical microscopy system 100, 200, when the vapor is not induced to the surface of the sample 60.

In S3, when the vapor-condensation-assisted device 20 is applied, the first opening 231 of the guide pipe 230 can be immersed into liquid and inhale some liquid into the vapor producing device 220. The liquid inhaled in the vapor producing device 220 is absorbed by the liquid absorbing material 222. When the vapor producing device 220 is heated by the heating layer 226, vapor is obtained and can flow with the air flow from the air bowling device 210 to the first opening 231. The vapor is induced to the surface of the sample 60. The liquid can be water or alcohol. In one embodiment, the liquid is water, the vapor is water vapor. When the vapor of water reaching the sample 60, the vapor of water would condense into micro-droplets which are attached to the sample 60. Under oblique illuminating light, the micro-droplets of water will act as scattering centers, appearing as bright dots under a dark-field optical microscope. Thus, the sample 60 is observed by the optical microscopy system 100, 200.

Figure 7:
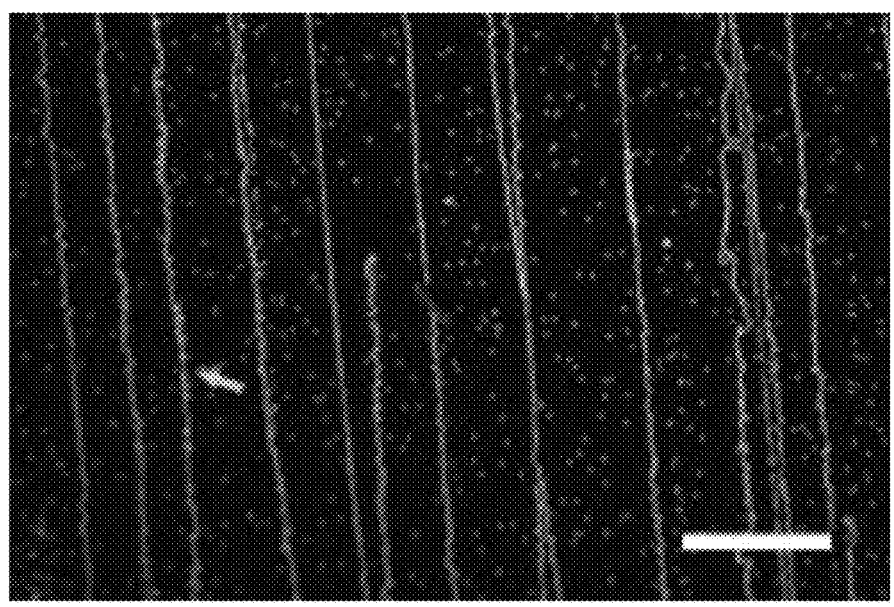
FIG. 7 is an optical microscopy image of the carbon nanotubes on the substrate by the optical microscopy system of one embodiment.
Figure 8:
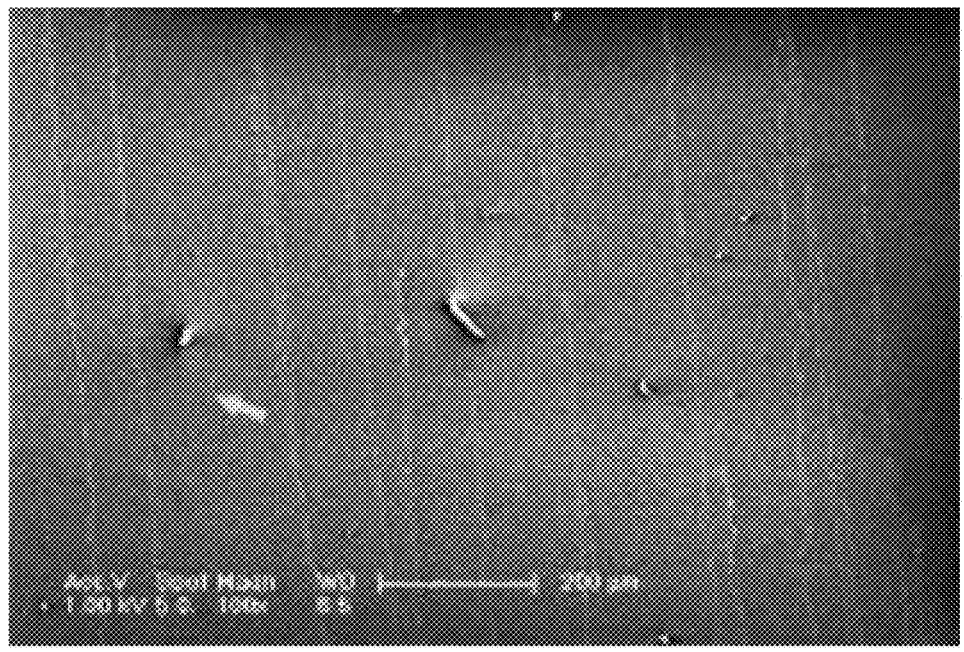
FIG. 8 is a Scanning Electron Microscope (SEM) image of the carbon nanotubes in FIG. 7.

Referring to FIG. 7, an optical microscopy image of carbon nanotubes 610 on the substrate 600 is taken by the above method via the optical microscopy system 100. The orientation of the carbon nanotubes 610 is clearly shown in FIG. 7. As a comparison, a SEM image of the carbon nanotubes 610 taken by a Scanning Electron Microscope is provided in FIG. 8. FIGS. 7 and 8 compare the optical microscopy image and the SEM image of the carbon nanotubes 610 on the same area of the substrate 600. It is evident that the optical microscopy image exactly shows the location and the morphology of the carbon nanotubes 610. In fact, there is a carbon nanotube visible in the optical microscopy image (indicated by the white arrow in FIG. 7), but invisible in the SEM image (where the white arrow locates in FIG. 8). This may be due to the special contrast mechanism of SEM.

In another embodiment, a method for observing nanostructures by an optical microscopy is provided. The method comprises the steps of:

S10, providing a sample 60 with a nanostructure;

S20, applying a cold source on the stage 110 of the optical microscope 10; and

S30, locating the sample 60 on the cold source to observe the sample 60 via the optical microscope 10 in an environment with vapor.

In S30, the cold source is used to decrease the temperature of the sample 60. The temperature of the sample 60 is lower than the temperature of environment when the sample 60 is located on the cold source. The vapor in the environment could condense on the surface of the sample 60, because the temperature of the sample 60 is lower than the temperature of environment. Therefore, the sample 60 can be observed by the optical microscope 10. The temperature of the cold source is under 0 C (centigrade). In one embodiment, the cold source is an ice block.

A method for observing nanostructures by an optical microscopy are provided according to one embodiment is provided. The method comprises steps of:

S100, providing a sample 60 with a nanostructure;

S200, applying a cold source on the stage 110 of the optical microscope 10;

S300, locating the sample 60 on the cold source; and

S400, applying a vapor to the sample 60 to observe the sample 60 via the optical microscope 10.

In S400, because the sample is located on the cold source, the temperature of the sample 60 is much lower than the temperature of the vapor. The vapor is easy to condense on the surface of the sample 60 under low temperature. The sample 60 can be easily observed by the optical microscope 10.

A technique to observe nanostructures by optical microscopy is developed with the help of water vapor condensation. Essentially, we do not directly observe the nanostructures themselves, but the condensation nuclei on them. The difference in the density and the type of the sub-nanometer condensation nuclei leads to different contrast under an optical microscope. In fact, the vapor molecule is not restricted to water. Any other vapor that meets the following conditions is acceptable. This simple, low-cost, and efficient optical microscopy system is applicable to a variety of nanostructures, even to functional groups, and does not induce any impurities to the specimens, which will pave the way for widespread applications.

Finally, it is to be understood that the above-described embodiments are intended to illustrate rather than limit the disclosure. Variations may be made to the embodiments without departing from the spirit of the disclosure as claimed. The above-described embodiments illustrate the scope of the disclosure but do not restrict the scope of the disclosure.

It is also to be understood that the above description and the claims drawn to a method may include some indication in reference to certain steps. However, the indication used is only to be viewed for identification purposes and not as a suggestion as to an order for the steps.

What is claimed is:

1. A method for observing nanostructures by optical microscopy comprising steps of:
    S1, providing a sample with a nanostructure, and a vapor-condensation-assisted optical microscopy system comprising a vapor-condensation-assisted device and an optical microscope comprises a stage, wherein the vapor-condensation-assisted device configured to provide vapor to the sample on the stage, and the nanostructure comprises carbon nanotubes;
    S2, locating the sample on the stage;
    S3, applying the vapor to the sample; and
    S4, directly observing the carbon nanotubes by optical microscopy.

2. The method as claimed in claim 1, wherein in step S1, the carbon nanotubes are horizontally aligned on a substrate.

3. The method as claimed in claim 1, wherein in step S2, the sample is located on a slide and the slide is put on the stage.

4. The method as claimed in claim 1, wherein the vapor-condensation-assisted device comprises an air blowing device, a vapor producing device and a guide pipe connected with each other; and the air blowing device blow air through the vapor producing device into the guide pipe.

5. The method as claimed in claim 4, wherein in step S3, the vapor is transported to a surface of the sample through the guide pipe.

6. The method as claimed in claim 5, wherein in step S3, the vapor is water vapor.

7. The method as claimed in claim 6, wherein in step S3, when the water vapor reaches the sample, the water vapor is condensed into micro-droplets which are attached to the surface of the sample.

8. The method as claimed in claim 7, where in step S3, the sample is observed by the optical microscope when the micro-droplets are formed on the surface of the sample.

9. The method as claimed in claim 1, wherein in step S2, a cold source is located on the stage under the sample.

10. The method as claimed in claim 9, wherein the temperature of the cold source is under 0 centigrade.

11. The method as claimed in claim 9, wherein the cold source is an ice block.

12. A method for observing nanostructures by optical microscopy comprising steps of:
S1, providing a sample with a nanostructure, and an optical microscope comprising a stage, wherein the nanostructure comprises carbon nanotubes;
S2, locating the sample on the stage; and
S3, inducing a vapor to a surface of the sample to directly observe the sample via the optical microscope.

13. The method as claimed in claim 12, wherein in step S1, the carbon nanotubes are horizontally aligned on a substrate.

14. The method as claimed in claim 12, wherein in step S2, the sample is located on a slide and the slide is put on the stage.

15. The method as claimed in claim 12 wherein in step S3, the vapor is transported to the surface of the sample.

16. The method as claimed in claim 12, wherein in step S3, the vapor is water vapor.

17. The method as claimed in claim 16, wherein in step S3, when the water vapor reaches the sample, the water vapor is condensed into micro-droplets which are attached to the surface of the sample.

18. The method as claimed in claim 17, where in step S3, the sample is observed by the optical microscope when the micro-droplets are formed on the surface of the sample.

19. The method as claimed in claim 1, wherein in step S2, a cold source is located on the stage and under the sample.

20. The method as claimed in claim 19, wherein the temperature of the cold source is under 0 centigrade.

* * * * *